US008034351B2

(12) United States Patent
Holgersson

(10) Patent No.: US 8,034,351 B2
(45) Date of Patent: Oct. 11, 2011

(54) MUCIN FUSION POLYPEPTIDE VACCINES, COMPOSITIONS AND METHODS OF USE THEREOF

(75) Inventor: Jan Holgersson, Huddinge (SE)

(73) Assignee: Recopharma AB, Huddinge (SE)

(*) Notice: Subject to any disclaimer, the term of this patent is extended or adjusted under 35 U.S.C. 154(b) by 490 days.

(21) Appl. No.: 10/421,199

(22) Filed: Apr. 22, 2003

(65) Prior Publication Data

US 2004/0002585 A1    Jan. 1, 2004

Related U.S. Application Data

(60) Provisional application No. 60/375,095, filed on Apr. 22, 2002.

(51) Int. Cl.
*A61K 39/00* (2006.01)
*A61K 39/385* (2006.01)
*A61K 39/395* (2006.01)
*A61K 51/00* (2006.01)

(52) U.S. Cl. .......... 424/192.1; 424/1.11; 424/1.41; 424/1.49; 424/1.53; 424/1.57; 424/130.1; 424/133.1; 424/134.1; 424/178.1; 424/183.1; 424/184.1; 424/185.1; 424/196.11; 424/197.11; 424/278.1

(58) Field of Classification Search .......... 424/1.11, 424/1.17, 130.1, 133.1, 134.1, 138.1, 139.1, 424/143.1, 147.1, 149.1, 150.1, 151.1, 157.1, 424/155.1, 156.1, 184.1, 185.1, 192.1, 193.1, 424/278.1; 530/300, 387.3; 435/69.7
See application file for complete search history.

(56) References Cited

U.S. PATENT DOCUMENTS

| 4,980,286 | A | 12/1990 | Morgan et al. | 435/172.3 |
|---|---|---|---|---|
| 5,225,538 | A | 7/1993 | Capon et al. | 530/387.3 |
| 5,428,130 | A | 6/1995 | Capon et al. | 530/350 |
| 5,455,165 | A | 10/1995 | Capon et al. | 435/64.7 |
| 5,514,582 | A | 5/1996 | Capon et al. | 435/252.3 |
| 5,516,964 | A | 5/1996 | Umansky et al. | 585/751 |
| 5,556,946 | A * | 9/1996 | Fujisawa et al. | 530/351 |
| 5,714,147 | A | 2/1998 | Capon et al. | 424/178.1 |
| 5,879,675 | A * | 3/1999 | Galili et al. | 424/93.1 |
| 6,136,310 | A | 10/2000 | Hanna et al. | 424/154.1 |
| 6,344,203 | B1 | 2/2002 | Sandrin et al. | 424/277.1 |
| 6,361,775 | B1 | 3/2002 | Galili et al. | 424/184.1 |
| 6,943,239 | B2 | 9/2005 | Holgersson et al. | |

FOREIGN PATENT DOCUMENTS

| EP | 415731 | 3/1991 |
|---|---|---|
| WO | WO 87/00329 | 1/1987 |
| WO | WO 90/07936 | 7/1990 |
| WO | WO 94/08598 | 4/1994 |
| WO | WO 95/24924 | 9/1995 |
| WO | WO 98/34957 | * 6/1998 |
| WO | WO 98/34957 | * 8/1998 |
| WO | WO 98/42750 | * 10/1998 |

OTHER PUBLICATIONS

Apostolopoulos et al. 1999. J. Mol. Med. Vo. 77: 427-436.*
Henion et al. 1997. Vaccine. vol. 15(11): 1174-1182.*
Jining et al. 1997. Transplanation. 1997. vol. 63(11):1673-1682 [prinout has pp. 1-14].*
Jining et al. 1997. Transplanation. 1997. vol. 63(11)1673-1682 [prinout has pp. 1-14].*
Henion et al. 1997. Vaccine. vol. 15(11): 1174-1182.*
Baldus et al. 2004. Critical Rev. Clin. Lab. Sci. vol. 41(2): 189-231.*
Henke et al (J. of Immunology. 2000. vol. 164:pp. 2131-41).*
R& D Systems: Technical Information; Cytokine Bulletin: Viral Cytokines (Jul. 1, 1998).*
Henion, et al., *Vaccine*, 15(11):1174-1182 (1997).
LaTemple, et al., *Subcell. Biochem.*, 32:361-379 (1999).
International Search Report for PCT/IB03/02207, mailing date: Dec. 5, 2003.
Baldari et al., "A novel leader peptide which allows efficient secretion of a fragment of human interleukin 1β in *Saccharomyces cerevisiae*", *EMBO J.*, 6:229-234 (1987).
Barany et al., "Solid-phase peptide synthesis: a silver anniversary report", *Intl. J. Peptide Protein Res.*, 30(6):705-739 (1987).
Galili et al., "Preparation of Autologous Leukemia and Lymphoma Vaccines Expressing α-Gal Epitopes", *J. Hematother. Stem Cell Res.*, 10(4):501-511 (2001).
Galili et al., "Natural anti-Gal antibody as a universal augmenter of autologous tumor vaccine immunogenicity", *Immunology Today*, 18(6):281-285 (1997).
GenBank Accession No. A57468, Oct. 12, 1999.
GenBank Accession No. AAA73558, Jul. 31, 1995.
GenBank Accession No. AJ417832, Oct. 21, 2008.
GenBank Accession No. AK016248, Sep. 19, 2008.
GenBank Accession No. BAB30163, Sep. 19, 2008.
GenBank Accession No. CAD10625, Oct. 21, 2008.
GenBank Accession No. L36150, Mar. 7, 1995.
GenBank Accession No. NM_009151, Jun. 7, 2009.
GenBank Accession No. NM_145650, Dec. 21, 2008.
GenBank Accession No. NP_033177, Jun. 7, 2009.
GenBank Accession No. NP_663625, Dec. 21, 2008.
GenBank Accession No. P50127, Jun. 16, 2009.
GenBank Accession No. XM_006867, Aug. 1, 2002.
GenBank Accession No. XM_140694, Oct. 8, 2002.
GenBank Accession No. XP_006867, Aug. 1, 2002. GenBank Accession No. XP_140694, Oct. 8, 2002.
Goldspiel et al., "Clinical Fronteirs: Human gene therapy", *Clin. Pharm.*, 12:488-505 (1993).
Kaiser et al., "Peptide and protein synthesis by segment synthesis-condensation", *Science*, 243:187-198 (1989).
Kappelmayer et al., "Identification of P-selectin glycoprotein ligand-1 as a useful marker in acute myeloid leukaemias",*Br. J. Heamatol.*, 115(4):903-909 (2001).
Kaufman et al., "Translational efficiency of polycistronic mRNAs and their utilization to express heterologous genes in mammalian cells", *EMBO J.*, 6:187-195 (1987).
Kent, "Chemical synthesis of peptides and proteins", *Ann. Rev. Biochem.*, 57:957-989 (1988).
Koller et al., "Inactivating the $^{\beta}$2-microglobin locus in mouse embryonic stem cells by homologous recombination", *Proc. Natl. Acad .Sci .U.S.A.*, 86:8932-8935 (1989).
Kurjan et al., "Structure of a yeast pheromone gene (MF α): a putative α-factor precursor contains four tandem copies of mature alpha-factor", *Cell*, 30(3):933-943 (1982).

(Continued)

*Primary Examiner* — Albert Navarro
*Assistant Examiner* — Ja'Na Hines
(74) *Attorney, Agent, or Firm* — Mintz Levin Cohn Ferris Glovsky and Popeo, P.C.; Ivor R. Elrifi; Cynthia A. Kozakiewicz

(57) ABSTRACT

The present invention provides compositions and methods for augmenting vaccine immunogenicity using mucin-immunoglobulin fusion proteins.

7 Claims, 7 Drawing Sheets

OTHER PUBLICATIONS

Loeffler et al., "Gene Transfer into Primary and Established Mammalian Cell lines with Lipopolyamine-Coated DNA", *Meth Enzymol.*, 217:599-618 (1993).

Lucklow et al., "High Level Expression of Nonfused Foreign Genes with *Autographa californica* nuclear Polyhedrosis Virus Expression Vectors", *Virology*, 170:31-39 (1989).

Reis et al., "Streptococcal Fc receptors. II. Comparison of the reactivity of a receptor from a group C streptococcus with staphylococcal protein A", *J. Immunol.*, 132:3098-3102 (1984).

Schultz et al., "Expression and secretion in yeast of a 400-kDa envelope glycoprotein derived from Epstein-Barr virus", *Gene*, 54(1):113-123 (1987).

Seed, "An LFA-3 cDNA encodes a phospholipid-linked membrane protein homologous to its receptor CD2", *Nature*, 329(6142):840-842 (1987).

Smith et al., "Production of human beta interferon in insect cells infected with a baculovirus expression vector." *Mol. Cell. Biol.*, 3:2156-2165 (1983).

Stemple et al., "Isolation of a Stem Cell for Neurons and Glia from the Mammalian Neural Crest", *Cell*, 71:973-985 (1992).

Wada et al., "Codon usage tabulated from the GenBank genetic sequence data", *Nucl. Acids Res.*, 20:2111-2118 (1992).

Wu et al., "Receptor-mediated in Vitro Gene Transformation by a Soluble DNA Carrier System", *J. Biol. Chem.*, 262:4429-4432 (1987).

* cited by examiner

MUCIN FUSION POLYPEPTIDE VACCINES, COMPOSITIONS AND METHODS OF USE THEREOF

RELATED APPLICATIONS

This application claims priority to U.S. Ser. No. 60/375,095, filed Apr. 22, 2002, the contents of which is incorporated herein by reference in its entirety.

FIELD OF THE INVENTION

The invention relates to compositions and methods of protein vaccines and their use in preventing and treating diseases such as cancer.

BACKGROUND OF THE INVENTION

The α-Gal (Galα1,3Galβ1,4GlcNAcβ1-R) carbohydrate epitope is expressed throughout the animal kingdom, with the notable exception of Old World monkeys, apes and humans. These species lack the epitope because of an inactivating mutation in the gene encoding the α1,3 galactosyltransferase responsible for its biosynthesis. In animals where it is present, it is carried both by lipids and on a variety of carrier proteins. Species lacking the epitope, e.g. humans, have antibodies recognizing α-Gal, possibly as a result of an immune response against bacterial capsular polysaccharides of the intestinal microflora. Anti-α-Gal (anti-Gal) antibodies are of all antibody classes and subclasses, and as much as 1% of human IgG has this specificity.

Mucins such as MUC1, and mucin-like molecules with highly O-glycosylated domains, such as P-selectin glycoprotein ligand-1 (PSGL-1), are extensively glycosylated high molecular weight (>200 kD) proteins and are targets for the α1,3 galactosyltransferase. Mucins are abundantly expressed in normal cells such as leukocytes and in many human cancers of epithelial origin.

SUMMARY OF THE INVENTION

The invention is based in part in the discovery that Galα1,3Gal-substituted proteins increase vaccine immunogenicity. Mucins, which are targets for the α1,3 galactosyltransferase, are particularly useful in vaccines.

The invention features a purified vaccine including an adjuvant polypeptide and one or more antigen moieties. The adjuvant polypeptide includes a first polypeptide and operably linked to a second polypeptide. The adjuvant polypeptide is a multimer such as a dimer.

The first polypeptide of the adjuvant polypeptide includes a mucin polypeptide and is glycosylated by an α1,3 galactosyltransferase. A mucin polypeptide includes for example, PSGL-1, MUC1, MUC2, MUC3, MUC4, MUC5a, MUC5b, MUC5c, MUC6, MUC11, MUC12, CD34, CD43, CD45, CD96, GlyCAM-1, MAdCAM, an extracellular region thereof, or a fragment thereof. The first polypeptide contains multiple Galα1, Gal epitopes. Preferably, the first polypeptide comprises more Galα1, 3Gal epitopes than a wild-type human P-selectin glycoprotein ligand-1 polypeptide. The second polypeptide of the adjuvant polypeptide includes a region of an immunoglobulin polypeptide.

The antigen is a for a example a virus, a bacteria or a fungus. For example, the antigen is Hepatitis C, HIV, Hepatitis B, Papilloma virus, Malaria, Tuberculosis, Herpes Simplex Virus, Chlamydia, or Influenza, or, a biological component thereof such as a peptide, protein, lipid carbohydrate, hormone or combination thereof. Alternatively, the antigen is a tumor associated antigen such as a breast, lung, colon, prostate, pancreatic, cervical or melanoma tumor-associated antigen. The antigen is operably linked to the adjuvant polypeptide. For example the antigen is covalently linked to the antigen Alternatively, the is associated with the adjuvant polypeptide non-covalently.

The second polypeptide includes a region of a heavy chain immunoglobulin polypeptide, such as an $F_c$ region or an $F_{ab}$ region.

The present invention further relates to an isolated nucleic acid encoding an adjuvant polypeptide, a vector including this isolated nucleic acid, and a cell comprising this vector. The vector further contains a nucleic acid encoding the antigen polypeptide.

The invention also features a methods of immunization. A subject is immunized by administering to subject in need thereof a vaccine according to the invention. In a further aspect, the present invention includes a method of preventing or alleviating a symptom of cancer in a subject by identifying a subject in need suffering from or at risk of developing cancer and administering to the subject a vaccine according to the invention. For example the subject is suffering from or at risk of developing melanoma, breast, lung, colon, prostate, pancreatic, cervical cancer. A subject suffering from or at risk of developing cancer is identified by methods know in the art for the particular disorder.

The invention further features methods of increasing antibody secretion or immune cell activation by contacting a cell with a vaccine according to the invention. The cell is a B cell or a T-cell.

Unless otherwise defined, all technical and scientific terms used herein have the same meaning as commonly understood by one of ordinary skill in the art to which this invention belongs. Although methods and materials similar or equivalent to those described herein can be used in the practice or testing of the present invention, suitable methods and materials are described below. All publications, patent applications, patents, and other references mentioned herein are incorporated by reference in their entirety. In case of conflict, the present specification, including definitions, will control. In addition, the materials, methods, and examples are illustrative only and not intended to be limiting.

Other features and advantages of the invention will be apparent from the following detailed description, and from the claims.

DETAILED DESCRIPTION OF THE INVENTION

Figure 1A:
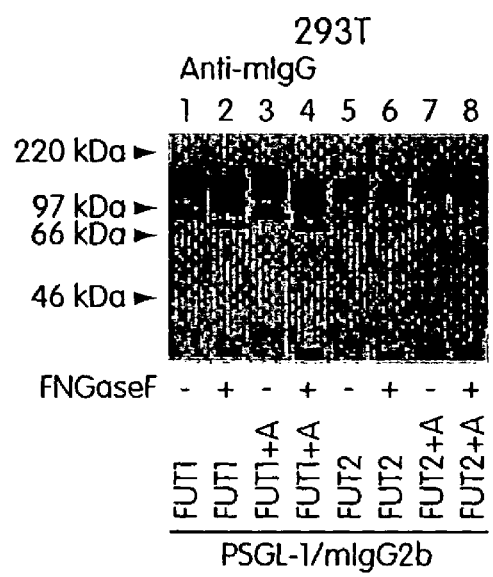
FIGS. 1A-D is a photograph of a Western blot of 1,3 gal-substituted PSGL-1/mIgG2b proteins. Six percent SDS-PAGE of proteins isolated from supernatants of COS cells transfected with vector alone (CDM8), PSGL-1/mIgG2b, or PSGL-1/mIgG2b and porcine α1,3GT expression plasmids. Anti-mouse IgG agarose beads were used for immunoaffinity purification of fusion proteins. Following extensive washing, the beads were boiled in sample buffer under reducing and non-reducing conditions to release absorbed proteins. Gels run in parallel were either silver stained, or used for electrophoretic transfer of separated proteins onto nitrocellulose membranes. These were subsequently probed with peroxidase-conjugated *Bandeireia simplicifolia* isolectin B4 lectin and visualized by chemiluminescence to detect Galα1,3Gal epitopes on immunopurified proteins. The gel migration length of molecular weight proteins of 220, 97 and 66 kDa is indicated on the left hand side.
Figure 1B:
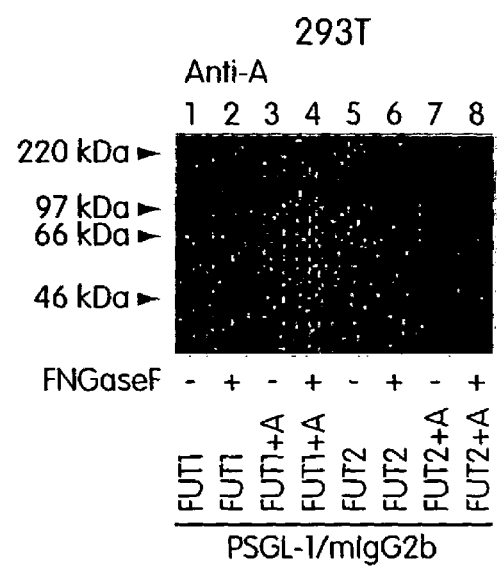
Figure 1C:
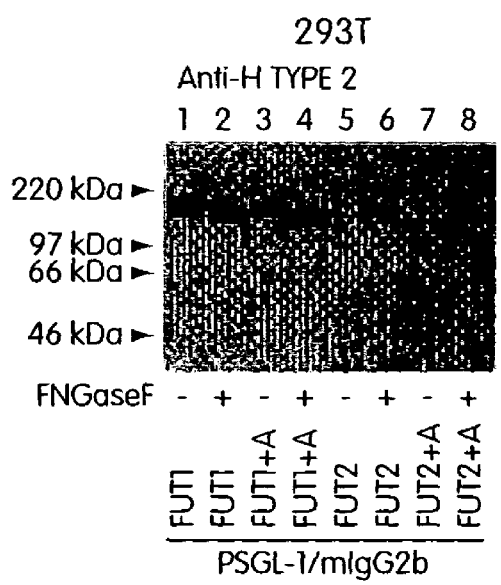
Figure 1D:
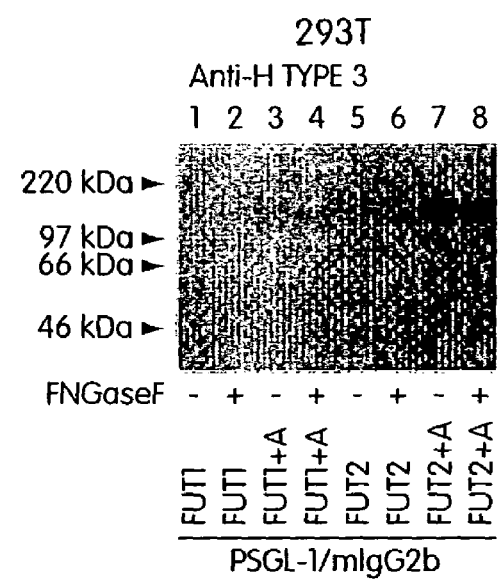

The invention is based in part on the discovery that mucin fusion proteins having Gal α1,3gal epitopes are effective adjuvants.

The natural anti-Gal antibody present in humans has been proposed as a universal augmentor of autologous tumor vaccine immunogenicity (Galili, 1997, Immunol Today 18(6): 281-5; Galili, 2001, J Hematother Stem Cell Res. 10(4):501-11). Anti-Gal antibodies binding to tumor cell membranes may facilitate Fc receptor- and complement receptor-mediated phagocytosis of tumor cell membranes by antigen presenting cells (APCs), and subsequently activate T helper and cytotoxic T lymphocytes by these APCs. Cytotoxic T lymphocytes primed against self MHC complexed with peptides derived from tumor-associated antigens would be generated and available for tumor cell cytolysis. The efficiency of the concept has been verified in a mouse tumor model in which α1,3 galactosyltransferase knockout mice were used as recipients of B16-B6 mouse melanoma cells. Vaccinating these mice with α1,3 galactosyltransferase-expressing stable transfectants of B16-B6 melanoma cells, but not with parental B16-B6 cells lacking the α-Gal epitope, protects them from a second challenge with live parental B16-BL6 cells.

As used herein, the following definitions are supplied in order to facilitate the understanding of this case. To the extent that the definitions vary from meanings known to those skilled in the art, the definitions below control.

By "mucin" is meant any polypeptide with one or more O-glycosylated domains, that are targets for the α1,3 galactosyltransferase.

By "biological component" is meant any compound created by or associated with a cell, tissue, bacteria, virus, or other biolical entity, including peptides, proteins, lipids, carbohydrates, hormones, or combinations thereof.

By "adjuvant compound" is meant any compound that increases an immunogenic response or the immunogenicity of an antigen or vaccine.

By "antigen" is meant any compound capable of inducing an immunogenic response.

By "immunoglobulin" is meant a any polypeptide or protein complex that is secreted by plasma cells and that functions as an antibody in the immune response by binding with a specific antigen. Immunoglobulins as used herein include IgA, IgD, IgE, IgG, and IgM. Regions of immunoglobulins include the Fe region and the Fab region, as well as the heavy chain or light chain immunoglobulins.

By "antigen presentation" is meant the expression of an antigen on the surface of a cell in association with one or more major hisocompatability complex class I or class II molecules. Antigen presentation is measured by methods known in the art. For example, antigen presentation is measured using an in vitro cellular assay as described in Gillis, et al., J. Immunol. 120: 2027 1978.

By "immunogenicity" is meant the ability of a substance to stimulate an immune response. Immunogenicity is measured, for example, by determining the presence of antibodies specific for the substance. The presence of antibodies is detected by methods know in the art, for example, an ELISA assay.

By "immune response" or "immunogenic response" is meant a cellular activity induced by an antigen, such as production of antibodies or presentation of antigens or antigen fragments.

By "proteolytic degradation" is meant degradation of the polypeptide by hydrolysis of the peptide bonds. No particular length is implied by the term "peptide." Proteolytic degradation is measured, for example, using gel electrophoresis.

The "cell" includes any cell capable of antigen presentation. For example, the cell is a somatic cell, a B-cell, a macrophage or a dendritic cell.

The invention provides adjuvant polypeptide fusion proteins (referred to herein as "mucin-Ig fusion proteins") containing a mucin polypeptide and a region of an immunoglobulin that are useful in combination with an antigen as vaccines. The vaccines are useful in methods of immunization in a subject, such as a human.

Vaccines

The vaccines of the invention include an adjuvant polypeptide and an antigen. The adjuvant polypeptide is a fusion protein, and the antigen is any compound or molecule to which an immune response is induced in a mammal.

Adjuvant Polypeptides

In various aspects the invention provides adjuvant fusion proteins that include a first polypeptide containing at least a portion of a glycoprotein, e.g., a mucin polypeptide operatively linked to a second polypeptide. By "at least a portion" is meant that the mucin polypeptide contains at least one mucin domain (e.g., an O-linked glycosylation site). As used herein, a "fusion protein" or "chimeric protein" includes at least a portion of a mucin polypeptide operatively linked to a non-mucin polypeptide. A "mucin polypeptide" refers to a polypeptide having a mucin domain. The mucin polypeptide has one, two, three, five, ten, twenty or more mucin domains. The mucin polypeptide is any glycoprotein characterized by a amino acid sequence substituted with O-glycans. For example, a mucin polypeptide has every second or third amino acid being a serine or threonine. The mucin polypeptide is a secreted protein. Alternatively, the mucin polypeptide is a cell surface protein.

Mucin domains are rich in the amino acids threonine, serine and proline, where the oligosaccharides are linked via N-acetylgalactosamine to the hydroxy amino acids (O-glycans). A mucin domain comprises or alternatively consists of an O-linked glycosylation site. A mucin domain has 1, 2, 3, 5, 10, 20, 50, 100 or more O-linked glycosylation sites. Alternatively, the mucin domain comprises or alternatively consists of a N-linked glycosylation site. A mucin polypeptide has 50%, 60%, 80%, 90%, 95% or 100% of its mass due to the glycan. Whereas a "non-mucin polypeptide" refers to a polypeptide of which at least less than 40% of its mass is due to glycans. A mucin polypeptide is any polypeptide encode for by a MUC genes (i.e., MUC1, MUC2, MUC3, MUC4, MUC5a, MUC5b, MUC5c, MUC6, MUC11, MUC12, etc.). Alternatively, a mucin polypeptide is P-selectin glycoprotein ligand 1 (PSGL-1), CD34, CD43, CD45, CD96, GlyCAM-1, MAdCAM, red blood cell glycophorins, glycocalicin, glycophorin, sialophorin, leukosialin, LDL-R, ZP3, and epiglycanin. Preferably, the mucin is PSGL-1.

The mucin polypeptide contains all or a portion of the mucin protein. Alternatively, the mucin protein includes the extracellular portion of the polypeptide. For example, the mucin polypeptide includes the extracellular portion of PSGL-1 or a portion thereof (e.g., amino acids 19-319 disclosed in GenBank Accession No. A57468). The mucin polypeptide also includes the signal sequence portion of PSGL-1 (e.g., amino acids 1-18), the transmembrane domain (e.g., amino acids 320-343), and the cytoplamic domain (e.g., amino acids 344-412).

The first polypeptide is glycosylated by a α1,3 galactosyltransferase. In some aspects, the first polypeptide is glycosylated by both a α1,3 galactosyltransferase and an α1,2 fucosyltransferase, a 1,3 N-acetylgalactosaminyltransferase, or another enzyme known to one of ordinary skill in the art to glycosylate polypeptides. Suitable sources for α1,3 galactosyltransferase include GenBank Accession Nos. AAA73558, L36150, BAB30163, AK016248, E46583 or P50127 and are incorporated herein by reference in their entirety.

The first polypeptide, and/or nucleic acids encoding the first polypeptide, is constructed using mucin encoding sequences are known in the art. Suitable sources for mucin polypeptides and nucleic acids encoding mucin polypeptides include GenBank Accession Nos. A57468, NP663625 and NM145650, CAD10625 and AJ417815, XP140694 and XM140694, XP006867 and XM006867 and NP00331777 and NM009151 respectively, and are incorporated herein by reference in their entirety.

The mucin polypeptide moiety is provided as a variant mucin polypeptide having a mutation in the naturally-occurring mucin sequence (wild type) that results in increased carbohydrate content (relative to the non-mutated sequence). For example, the variant mucin polypeptide comprised additional O-linked glycosylation sites compared to the wild-type mucin. Alternatively, the variant mucin polypeptide comprises an amino acid sequence mutations that results in an increased number of serine, threonine or proline residues as compared to a wild type mucin polypeptide. This increased carbohydrate content is assessed by determining the protein to carbohydrate ratio of the mucin by methods know to those skilled in the art.

The mucin polypeptide moiety is provided as a variant mucin polypeptide having mutations in the naturally-occurring mucin sequence (wild type) that results in a mucin sequence more resistant to proteolysis (relative to the non-mutated sequence).

The first polypeptide includes full-length PSGL-1. Alternatively, the first polypeptide comprise less than full-length PSGL-1 polypeptide such as the extracellular portion of PSGL-1. For example the first polypeptide less than 400 amino acids in length, e.g., less than or equal to 300, 250, 150, 100, 50, or 25 amino acids in length. Exemplary PSGL-1 polypeptide and nucleic acid sequences include GenBank Access No: A57468; XP006867; XM006867; XP140694 and XM140694.

The second polypeptide includes at least a region of an immunoglobulin polypeptide. "At least a region" is meant to include any portion of an immunoglobulin molecule, such as the light chain, heavy chain, FC region, Fab region, Fv region or any fragment thereof. Immunoglobulin fusion polypeptide are known in the art and are described in e.g., U.S. Pat. Nos. 5,516,964; 5,225,538; 5,428,130; 5,514,582; 5,714,147; and 5,455,165.

The second polypeptide comprises a full-length immunoglobulin polypeptide. Alternatively, the second polypeptide comprise less than full-length immunoglobulin polypeptide, e.g., a heavy chain, light chain, Fab, $Fab_2$, Fv, or Fe. Preferably, the second polypeptide includes the heavy chain of an immunoglobulin polypeptide. More preferably the second polypeptide includes the Fe region of an immunoglobulin polypeptide.

In another aspect of the invention the second polypeptide has less effector function that the effector function of a Fe region of a wild-type immunoglobulin heavy chain. Fe effector function includes for example, Fe receptor binding, complement fixation and T cell depleting activity. (see for example, U.S. Pat. No. 6,136,310) Methods of assaying T cell depleting activity, Fe effector function, and antibody stability are known in the art. In one embodiment the second polypeptide has low or no affinity for the Fe receptor. In an alternative embodiment, the second polypeptide has low or no affinity for complement protein C1q.

Antigens

The vaccines of the present invention also include an antigen. An "antigen" includes any compound to which an immune response is desired. An antigen includes any substance that, when introduced into the body, stimulates an immune response, such as the production of an antibody from a B cell, activation and expansion of T cells, and cytokine expression (e.g., interleukins). By a "B cell" or "B lymphocyte" is meant an immune cell that, when activated, is responsible for the production of antibodies. By a "T cell" or "T lymphocyte" is meant a member of a class of lymphocytes, further defined as cytotoxic T cells and helper T cells. T cells regulate and coordinate the overall immune response, identifying the epitopes that mark the antigens, and attacking and destroying the diseased cells they recognize as foreign. Antigens include for example, toxins, bacteria, foreign blood cells, and the cells of transplanted organs. Preferably, the antigen is Hepatitis C, HIV, Hepatitis B, Papilloma virus, Malaria, Tuberculosis, Herpes Simplex Virus, Chlamydia, and Influenza, or a biological component thereof, for example, a viral or bacterial polypeptide. In embodiments of the invention the adjuvant polypeptide is covalently linked to the antigen.

The vaccine includes an adjuvant polypeptide operably linked to an antigen. "Operatively linked" is intended to indicate that the first and second polypeptides of the adjuvant polypeptide are chemically linked (e.g., via a covalent bond such as a peptide bond) in a manner that allows for O-linked glycosylation of the first polypeptide. When used to refer to nucleic acids encoding a fusion polypeptide, the term operatively linked means that a nucleic acid encoding the mucin polypeptide and the non-mucin polypeptide are fused in-frame to each other. The non-mucin polypeptide is fused to the N-terminus or C-terminus of the mucin polypeptide. The antigen is operably linked to the adjuvant polypeptide. For example, the adjuvant polypeptide is linked to the antigen via a covalent bond such as a peptide bond. The antigen is fused to the N-terminus or C-terminus of the mucin polypeptide. Alternatively, the antigen is fused to an internal amino acid of the mucin polypeptide. By "internal amino acid" is meant an amino acid that is not at the N-terminal or C-terminal of a polypeptide. Similarly, the antigen is operably linked to the second polypeptide of the adjuvant polypeptide, most typically via a covalent bond such as a peptide bond. The antigen is fused to the N-terminus or C-terminus of the second polypeptide of the adjuvant polypeptide. Alternatively, the antigen is fused to an internal amino acid of the second polypeptide of the adjuvant polypeptide.

The vaccine or adjuvant polypeptide is linked to one or more additional moieties. For example, the vaccine may additionally be linked to a GST fusion protein in which the mucin-Ig fusion protein sequences are fused to the C-terminus of the GST (i.e., glutathione S-transferase) sequences. Such fusion proteins can facilitate the purification of the vaccine or adjuvant polypeptide. Alternatively, the vaccine or adjuvant polypeptide may additionally be linked to a solid support. Various solid support are know to those skilled in the art. Such compositions can facilitate removal of anti-blood group antibodies. For example, the vaccine or adjuvant polypeptide is linked to a particle made of, e.g., metal compounds, silica, latex, polymeric material; a microtiter plate; nitrocellulose, or nylon or a combination thereof.

The fusion protein is includes a heterologous signal sequence (i.e., a polypeptide sequence that is not present in a polypeptide encoded by a mucin nucleic acid) at its N-terminus. For example, the native mucin signal sequence is removed and replaced with a signal sequence from another protein. In certain host cells (e.g., mammalian host cells), expression and/or secretion of polypeptide is increased through use of a heterologous signal sequence.

A chimeric or fusion protein of the invention is produced by standard recombinant DNA techniques. For example, DNA fragments coding for the different polypeptide sequences are ligated together in-frame in accordance with conventional techniques, e.g., by employing blunt-ended or stagger-ended termini for ligation, restriction enzyme digestion to provide for appropriate termini, filling-in of cohesive ends as appropriate, alkaline phosphatase treatment to avoid undesirable joining, and enzymatic ligation. In another embodiment, the fusion gene is synthesized by conventional techniques including automated DNA synthesizers. Alternatively, PCR amplification of gene fragments is carried out using anchor primers that give rise to complementary overhangs between two consecutive gene fragments that can subsequently be annealed and reamplified to generate a chimeric gene sequence (see, for example, Ausubel et al. (eds.) CURRENT PROTOCOLS IN MOLECULAR BIOLOGY, John Wiley & Sons, 1992). Moreover, many expression vectors are commercially available that encode a fusion moiety (e.g., an Fc region of an immunoglobulin heavy chain). A mucin-encoding nucleic acid is cloned into such an expression vector such that the fusion moiety is linked in-frame to the immunoglobulin protein.

Vaccine polypeptides or adjuvant polypeptides may exist as oligomers, such as dimers, trimers or pentamers. Preferably, the vaccine or adjuvant polypeptide is a dimer. More preferably, the vaccine or adjuvant polypeptide is a dimeric PSGL-1 protein, or the extracellular region thereof.

Expression of Mucin-Immunoglobulin Fusion Protein-Containing Vaccines

Another aspect of the invention pertains to vectors, preferably expression vectors, containing a nucleic acid encoding mucin polypeptides, or derivatives, fragments, analogs or homologs thereof. In various aspects the vector contains a nucleic acid encoding a mucin polypeptide operably linked to an nucleic acid encoding an immunoglobulin polypeptide, or derivatives, fragments analogs or homologs thereof. Additionally, the vector comprises a nucleic acid encoding a $\alpha 1,3$ galactosyltransferase, or similar enzyme useful to glycosylate a polypeptide, and a nucleic acid encoding an antigen. As used herein, the term "vector" refers to a nucleic acid molecule capable of transporting another nucleic acid to which it has been linked. One type of vector is a "plasmid", which refers to a circular double stranded DNA loop into which additional DNA segments are ligated. Another type of vector is a viral vector, wherein additional DNA segments are ligated into the viral genome. Certain vectors are capable of autonomous replication in a host cell into which they are introduced (e.g., bacterial vectors having a bacterial origin of replication and episomal mammalian vectors). Other vectors (e.g., non-episomal mammalian vectors) are integrated into the genome of a host cell upon introduction into the host cell, and thereby are replicated along with the host genome. Moreover, certain vectors are capable of directing the expression of genes to which they are operatively-linked. Such vectors are referred to herein as "expression vectors". In general, expression vectors of utility in recombinant DNA techniques are often in the form of plasmids. In the present specification, "plasmid" and "vector" is used interchangeably as the plasmid is the most commonly used form of vector. However, the invention is intended to include such other forms of expression vectors, such as viral vectors (e.g., replication defective retroviruses, adenoviruses and adeno-associated viruses), which serve equivalent functions.

The recombinant expression vectors of the invention comprise a nucleic acid of the invention in a form suitable for expression of the nucleic acid in a host cell, which means that the recombinant expression vectors include one or more regulatory sequences, selected on the basis of the host cells to be used for expression, that is operatively-linked to the nucleic acid sequence to be expressed. Within a recombinant expression vector, "operably-linked" is intended to mean that the nucleotide sequence of interest is linked to the regulatory sequence(s) in a manner that allows for expression of the nucleotide sequence (e.g., in an in vitro transcription/translation system or in a host cell when the vector is introduced into the host cell).

The term "regulatory sequence" is intended to includes promoters, enhancers and other expression control elements (e.g., polyadenylation signals). Such regulatory sequences are described, for example, in Goeddel, GENE EXPRESSION TECHNOLOGY: METHODS IN ENZYMOLOGY 185, Academic Press, San Diego, Calif. (1990). Regulatory sequences include those that direct constitutive expression of a nucleotide sequence in many types of host cell and those that direct expression of the nucleotide sequence only in certain host cells (e.g., tissue-specific regulatory sequences). It will be appreciated by those skilled in the art that the design of the expression vector can depend on such factors as the choice of the host cell to be transformed, the level of expression of protein desired, etc. The expression vectors of the invention are introduced into host cells to thereby produce proteins or peptides, including fusion proteins or peptides, encoded by nucleic acids as described herein (e.g., mucin-Ig fusion polypeptides, mutant forms of MUCIN-IG fusion polypeptides, etc.).

The recombinant expression vectors of the invention are designed for expression of mucin-Ig fusion polypeptides in prokaryotic or eukaryotic cells. For example, vaccines containing mucin-Ig fusion polypeptides are expressed in bacterial cells such as *Escherichia coli*, insect cells (using baculovirus expression vectors) yeast cells or mammalian cells. Suitable host cells are discussed further in Goeddel, GENE EXPRESSION TECHNOLOGY: METHODS IN ENZYMOLOGY 185, Academic Press, San Diego, Calif. (1990). Alternatively, the recombinant expression vector is transcribed and translated in vitro, for example using T7 promoter regulatory sequences and T7 polymerase.

Expression of proteins in prokaryotes is most often carried out in *Escherichia coli* with vectors containing constitutive or inducible promoters directing the expression of either fusion or non-fusion proteins. Fusion vectors add a number of amino acids to a protein encoded therein, usually to the amino terminus of the recombinant protein. Such fusion vectors typically serve three purposes: (i) to increase expression of recombinant protein; (ii) to increase the solubility of the recombinant protein; and (iii) to aid in the purification of the recombinant protein by acting as a ligand in affinity purification. Often, in fusion expression vectors, a proteolytic cleavage site is introduced at the junction of the fusion moiety and the recombinant protein to enable separation of the recombinant protein from the fusion moiety subsequent to purification of the fusion protein. Such enzymes, and their cognate recognition sequences, include Factor Xa, thrombin and enterokinase. Typical fusion expression vectors include pGEX (Pharmacia Biotech Inc; Smith and Johnson, 1988. *Gene* 67: 31-40), pMAL (New England Biolabs, Beverly, Mass.) and pRIT5 (Pharmacia, Piscataway, N.J.) that fuse glutathione S-transferase (GST), maltose E binding protein, or protein A, respectively, to the target recombinant protein.

Examples of suitable inducible non-fusion *E. coli* expression vectors include pTrc (Amrann et al., (1988) *Gene* 69:301-315) and pET 11d (Studier et al., GENE EXPRESSION TECHNOLOGY: METHODS IN ENZYMOLOGY 185, Academic Press, San Diego, Calif. (1990) 60-89).

One strategy to maximize recombinant protein expression in *E. coli* is to express the protein in a host bacteria with an impaired capacity to proteolytically cleave the recombinant protein. See, e.g., Gottesman, GENE EXPRESSION TECHNOLOGY: METHODS IN ENZYMOLOGY 185, Academic Press, San Diego, Calif. (1990) 119-128. Another strategy is to alter the nucleic acid sequence of the nucleic acid to be inserted into an expression vector so that the individual codons for each amino acid are those preferentially utilized in *E. coli* (see, e.g., Wada, et al., 1992. *Nucl. Acids Res.* 20: 2111-2118). Such alteration of nucleic acid sequences of the invention is carried out by standard DNA synthesis techniques.

The vaccine or adjuvant polypeptide expression vector is a yeast expression vector. Examples of vectors for expression in yeast *Saccharomyces cerivisae* include pYepSec1 (Baldari, et al., 1987. *EMBO J.* 6: 229-234), pMFa (Kurjan and Herskowitz, 1982. *Cell* 30: 933-943), pJRY88 (Schultz et al., 1987. Gene 54: 113-123), pYES2 (Invitrogen Corporation, San Diego, Calif.), and picZ (Invitrogen Corp, San Diego, Calif.).

Alternatively, vaccine or adjuvant polypeptides are expressed in insect cells using baculovirus expression vectors. Baculovirus vectors available for expression of proteins in cultured insect cells (e.g., SF9 cells) include the pAc series (Smith, et al., 1983. *Mol. Cell. Biol.* 3: 2156-2165) and the pVL series (Lucklow and Summers, 1989. *Virology* 170: 31-39).

A nucleic acid of the invention is expressed in mammalian cells using a mammalian expression vector. Examples of mammalian expression vectors include pCDM8 (Seed, 1987. *Nature* 329: 840) and pMT2PC (Kaufman, et al., 1987. *EMBO J.* 6: 187-195). When used in mammalian cells, the expression vector's control functions are often provided by viral regulatory elements. For example, commonly used promoters are derived from polyoma, adenovirus 2, cytomegalovirus, and simian virus 40. For other suitable expression systems for both prokaryotic and eukaryotic cells see, e.g., Chapters 16 and 17 of Sambrook, et al., MOLECULAR CLONING: A LABORATORY MANUAL. 2nd ed., Cold Spring Harbor Laboratory, Cold Spring Harbor Laboratory Press, Cold Spring Harbor, N.Y., 1989.

The invention pertains to host cells into which a recombinant expression vector of the invention has been introduced. The terms "host cell" and "recombinant host cell" are used interchangeably herein. It is understood that such terms refer not only to the particular subject cell but also to the progeny or potential progeny of such a cell. Because certain modifications may occur in succeeding generations due to either mutation or environmental influences, such progeny may not, in fact, be identical to the parent cell, but are still included within the scope of the term as used herein.

A host cell is any prokaryotic or eukaryotic cell. For example, the adjuvant polypeptides and or vaccines are expressed in bacterial cells such as *E. coli*, insect cells, yeast or mammalian cells (such as human, Chinese hamster ovary cells (CHO) or COS cells). Other suitable host cells are known to those skilled in the art.

Vector DNA is introduced into prokaryotic or eukaryotic cells via conventional transformation or transfection techniques. As used herein, the terms "transformation" and "transfection" are intended to refer to a variety of art-recognized techniques for introducing foreign nucleic acid (e.g., DNA) into a host cell, including calcium phosphate or calcium chloride co-precipitation, DEAE-dextran-mediated transfection, lipofection, or electroporation. Suitable methods for transforming or transfecting host cells are found in Sambrook, et al. (MOLECULAR CLONING: A LABORATORY MANUAL. 2nd ed., Cold Spring Harbor Laboratory, Cold Spring Harbor Laboratory Press, Cold Spring Harbor, N.Y., 1989), and other laboratory manuals.

For stable transfection of mammalian cells, it is known that, depending upon the expression vector and transfection technique used, only a small fraction of cells may integrate the foreign DNA into their genome. In order to identify and select these integrants, a gene that encodes a selectable marker (e.g., resistance to antibiotics) is generally introduced into the host cells along with the gene of interest. Various selectable markers include those that confer resistance to drugs, such as G418, hygromycin and methotrexate. Nucleic acid encoding a selectable marker is introduced into a host cell on the same vector as that encoding the vaccines containing mucin fusion polypeptides, or are introduced on a separate vector. Cells stably transfected with the introduced nucleic acid are identified by drug selection (e.g., cells that have incorporated the selectable marker gene will survive, while the other cells die).

A host cell of the invention, such as a prokaryotic or eukaryotic host cell in culture, is used to produce (i.e., express) adjuvant polypeptides and or vaccines. Accordingly, the invention further provides methods for producing adjuvant polypeptides and or vaccines using the host cells of the invention. The method includes culturing the host cell of invention (into which a recombinant expression vector encoding adjuvant polypeptides and or vaccines has been introduced) in a suitable medium such that adjuvant polypeptides and or vaccines s is produced. The method further includes isolating adjuvant polypeptides and or vaccines from the medium or the host cell.

The vaccines containing mucin-Ig fusion polypeptides are isolated and purified in accordance with conventional conditions, such as extraction, precipitation, chromatography, affinity chromatography, electrophoresis or the like. For example, the vaccines are purified by passing a solution through a column which contains immobilized protein A or protein G which selectively binds the Fc portion of the fusion protein. See, for example, Reis, K. J., et al., *J. Immunol.* 132:3098-3102 (1984); PCT Application, Publication No. WO87/00329. The fusion polypeptide may the be eluted by treatment with a chaotropic salt or by elution with aqueous acetic acid (1 M).

Alternatively, adjuvant polypeptides and or vaccine according to the invention are chemically synthesized using methods known in the art. Chemical synthesis of polypeptides is described in, e.g., A variety of protein synthesis methods are common in the art, including synthesis using a peptide synthesizer. See, e.g., *Peptide Chemistry, A Practical Textbook*, Bodansky, Ed. Springer-Verlag, 1988; Merrifield, *Science* 232: 241-247 (1986); Barany, et al, *Intl. J. Peptide Protein Res.* 30: 705-739 (1987); Kent, *Ann. Rev. Biochem.* 57:957-989 (1988), and Kaiser, et al, *Science* 243: 187-198 (1989). The polypeptides are purified so that they are substantially free of chemical precursors or other chemicals using standard peptide purification techniques. The language "substantially free of chemical precursors or other chemicals" includes preparations of peptide in which the peptide is separated from chemical precursors or other chemicals that are involved in the synthesis of the peptide. In one embodiment, the language "substantially free of chemical precursors or other chemicals" includes preparations of peptide having less than about 30% (by dry weight) of chemical precursors or non-peptide chemicals, more preferably less than about 20% chemical precursors or non-peptide chemicals, still more preferably less than about 10% chemical precursors or non-peptide chemicals, and most preferably less than about 5% chemical precursors or non-peptide chemicals.

Chemical synthesis of polypeptides facilitates the incorporation of modified or unnatural amino acids, including D-amino acids and other small organic molecules. Replacement of one or more L-amino acids in a peptide with the corresponding D-amino acid isoforms is used to increase the resistance of peptides to enzymatic hydrolysis, and to enhance one or more properties of biologically active peptides, i.e., receptor binding, functional potency or duration of action. See, e.g., Doherty, et al., 1993. *J. Med. Chem.* 36: 2585-2594; Kirby, et al., 1993. *J. Med. Chem.* 36:3802-3808; Morita, et al., 1994. *FEBS Lett.* 353: 84-88; Wang, et al., 1993. *Int. J. Pept. Protein Res.* 42: 392-399; Fauchere and Thiunieau, 1992. *Adv. Drug Res.* 23: 127-159.

Introduction of covalent cross-links into a peptide sequence can conformationally and topographically constrain the polypeptide backbone. This strategy is used to develop peptide analogs of the fusion polypeptides with increased potency, selectivity and stability. Because the conformational entropy of a cyclic peptide is lower than its linear counterpart, adoption of a specific conformation may occur with a smaller decrease in entropy for a cyclic analog than for an acyclic analog, thereby making the free energy for binding more favorable. Macrocyclization is often accomplished by forming an amide bond between the peptide N- and C-termini, between a side chain and the N- or C-terminus [e.g., with $K_3Fe(CN)_6$ at pH 8.5] (Samson et al., *Endocrinology*, 137: 5182-5185 (1996)), or between two amino acid side chains. See, e.g., DeGrado, *Adv Protein Chem*, 39: 51-124 (1988). Disulfide bridges are also introduced into linear sequences to reduce their flexibility. See, e.g., Rose, et al., *Adv Protein Chem*, 37: 1-109 (1985); Mosberg et al., *Biochem Biophys Res Commun*, 106: 505-512 (1982). Furthermore, the replacement of cysteine residues with penicillamine (Pen, 3-mercapto-(D) valine) has been used to increase the selectivity of some opioid-receptor interactions. Lipkowski and Carr, *Peptides: Synthesis, Structures, and Applications*, Gutte, ed., Academic Press pp. 287-320 (1995).

Pharmaceutical Compositions

The vaccines and fusion peptides and nucleic acids of the invention can be formulated in pharmaceutical compositions. These compositions may comprise, in addition to one of the above substances, a pharmaceutically acceptable excipient, carrier, buffer, stabiliser or other materials well known to those skilled in the art. Such materials should be non-toxic and should not interfere with the efficacy of the active ingredient. The precise nature of the carrier or other material may depend on the route of administration, e.g. oral, intravenous, cutaneous or subcutaneous, nasal, intramuscular, intraperitoneal or patch routes.

Pharmaceutical compositions for oral administration may be in tablet, capsule, powder or liquid form. A tablet may include a solid carrier such as gelatin or an adjuvant. Liquid pharmaceutical compositions generally include a liquid carrier such as water, petroleum, animal or vegetable oils, mineral oil or synthetic oil. Physiological saline solution, dextrose or other saccharide solution or glycols such as ethylene glycol, propylene glycol or polyethylene glycol may be included.

For intravenous, cutaneous or subcutaneous injection, or injection at the site of affliction, the active ingredient will be in the form of a parenterally acceptable aqueous solution which is pyrogen-free and has suitable pH, isotonicity and stability. Those of relevant skill in the art are well able to prepare suitable solutions using, for example, isotonic vehicles such as Sodium Chloride Injection, Ringer's Injection, Lactated Ringer's Injection. Preservatives, stabilisers, buffers, antioxidants and/or other additives may be included, as required.

Whether it is a polypeptide, peptide, or nucleic acid molecule, other pharmaceutically useful compound according to the present invention that is to be given to an individual, administration is preferably in a "prophylactically effective amount" or a "therapeutically effective amount" (as the case may be, although prophylaxis may be considered therapy), this being sufficient to show benefit to the individual. The actual amount administered, and rate and time-course of administration, will depend on the nature and severity of what is being treated. Prescription of treatment, e.g. decisions on dosage etc, is within the responsibility of general practitioners and other medical doctors, and typically takes account of the disorder to be treated, the condition of the individual patient, the site of delivery, the method of administration and other factors known to practitioners. Examples of the techniques and protocols mentioned above can be found in REMINGTON'S PHARMACEUTICAL SCIENCES, 16th edition, Osol, A. (ed), 1980.

Alternatively, targeting therapies may be used to deliver the active agent more specifically to certain types of cell, by the use of targeting systems such as antibody or cell specific ligands. Targeting may be desirable for a variety of reasons;

for example if the agent is unacceptably toxic, or if it would otherwise require too high a dosage, or if it would not otherwise be able to enter the target cells.

Instead of administering these agents directly, they could be produced in the target cells by expression from an encoding gene introduced into the cells, e.g. in a viral vector (a variant of the VDEPT technique—see below). The vector could be targeted to the specific cells to be treated, or it could contain regulatory elements, which are switched on more or less selectively by the target cells.

Alternatively, the agent could be administered in a precursor form, for conversion to the active form by an activating agent produced in, or targeted to, the cells to be treated. This type of approach is sometimes known as ADEPT or VDEPT; the former involving targeting the activating agent to the cells by conjugation to a cell-specific antibody, while the latter involves producing the activating agent, e.g. a vaccine or fusion protein, in a vector by expression from encoding DNA in a viral vector (see for example, EP-A-415731 and WO 90/07936).

In a specific embodiment of the present invention, nucleic acids include a sequence that encodes a vaccine, or functional derivatives thereof, are administered to modulate immune cell activation by way of gene therapy. In more specific embodiments, a nucleic acid or nucleic acids encoding a vaccine or fusion protein, or functional derivatives thereof, are administered by way of gene therapy. Gene therapy refers to therapy that is performed by the administration of a specific nucleic acid to a subject. In this embodiment of the present invention, the nucleic acid produces its encoded peptide(s), which then serve to exert a therapeutic effect by modulating function of the disease or disorder. Any of the methodologies relating to gene therapy available within the art may be used in the practice of the present invention. See e.g., Goldspiel, et al., 1993. *Clin Pharm* 12: 488-505.

In a preferred embodiment, the Therapeutic comprises a nucleic acid that is part of an expression vector expressing any one or more of the vaccines, fusion proteins, or fragments, derivatives or analogs thereof, within a suitable host. In a specific embodiment, such a nucleic acid possesses a promoter that is operably-linked to coding region(s) of a fusion protein. The promoter may be inducible or constitutive, and, optionally, tissue-specific. In another specific embodiment, a nucleic acid molecule is used in which coding sequences (and any other desired sequences) are flanked by regions that promote homologous recombination at a desired site within the genome, thus providing for intra-chromosomal expression of nucleic acids. See e.g., Koller and Smithies, 1989. *Proc Natl Acad Sci USA* 86: 8932-8935.

Delivery of the Therapeutic nucleic acid into a patient may be either direct (i.e., the patient is directly exposed to the nucleic acid or nucleic acid-containing vector) or indirect (i.e., cells are first transformed with the nucleic acid in vitro, then transplanted into the patient). These two approaches are known, respectively, as in vivo or ex vivo gene therapy. In a specific embodiment of the present invention, a nucleic acid is directly administered in vivo, where it is expressed to produce the encoded product. This may be accomplished by any of numerous methods known in the art including, e.g., constructing the nucleic acid as part of an appropriate nucleic acid expression vector and administering the same in a manner such that it becomes intracellular (e.g., by infection using a defective or attenuated retroviral or other viral vector; see U.S. Pat. No. 4,980,286); directly injecting naked DNA; using microparticle bombardment (e.g., a "Gene Gun®; Biolistic, DuPont); coating the nucleic acids with lipids; using associated cell-surface receptors/transfecting agents; encapsulating in liposomes, microparticles, or microcapsules; administering it in linkage to a peptide that is known to enter the nucleus; or by administering it in linkage to a ligand predisposed to receptor-mediated endocytosis (see, e.g., Wu and Wu, 1987. *J Biol Chem* 262: 4429-4432), which can be used to "target" cell types that specifically express the receptors of interest, etc.

An additional approach to gene therapy in the practice of the present invention involves transferring a gene into cells in in vitro tissue culture by such methods as electroporation, lipofection, calcium phosphate-mediated transfection, viral infection, or the like. Generally, the method of transfer includes the concomitant transfer of a selectable marker to the cells. The cells are then placed under selection pressure (e.g., antibiotic resistance) so as to facilitate the isolation of those cells that have taken up, and are expressing, the transferred gene. Those cells are then delivered to a patient. In a specific embodiment, prior to the in vivo administration of the resulting recombinant cell, the nucleic acid is introduced into a cell by any method known within the art including, e.g., transfection, electroporation, microinjection, infection with a viral or bacteriophage vector containing the nucleic acid sequences of interest, cell fusion, chromosome-mediated gene transfer, microcell-mediated gene transfer, spheroplast fusion, and similar methodologies that ensure that the necessary developmental and physiological functions of the recipient cells are not disrupted by the transfer. See e.g., Loeffler and Behr, 1993. *Meth Enzymol* 217: 599-618. The chosen technique should provide for the stable transfer of the nucleic acid to the cell, such that the nucleic acid is expressible by the cell. Preferably, the transferred nucleic acid is heritable and expressible by the cell progeny.

In preferred embodiments of the present invention, the resulting recombinant cells may be delivered to a patient by various methods known within the art including, e.g., injection of epithelial cells (e.g., subcutaneously), application of recombinant skin cells as a skin graft onto the patient, and intravenous injection of recombinant blood cells (e.g., hematopoietic stem or progenitor cells). The total amount of cells that are envisioned for use depend upon the desired effect, patient state, and the like, and may be determined by one skilled within the art.

Cells into which a nucleic acid can be introduced for purposes of gene therapy encompass any desired, available cell type, and may be xenogeneic, heterogeneic, syngeneic, or autogeneic. Cell types include, but are not limited to, differentiated cells such as epithelial cells, endothelial cells, keratinocytes, fibroblasts, muscle cells, hepatocytes and blood cells, or various stem or progenitor cells, in particular embryonic heart muscle cells, liver stem cells (International Patent Publication WO 94/08598), neural stem cells (Stemple and Anderson, 1992, *Cell* 71: 973-985), hematopoietic stem or progenitor cells, e.g. as obtained from bone marrow, umbilical cord blood, peripheral blood, fetal liver, and the like. In a preferred embodiment, the cells utilized for gene therapy are autologous to the patient.

The vaccines of the present invention also include one or more adjuvant compounds. Adjuvant compounds are useful in that they enhance long term release of the vaccine by functioning as a depot. Long term exposure to the vaccine should increase the length of time the immune system is presented with the antigen for processing as well as the duration of the antibody response. The adjuvant compound also interacts with immune cells, e.g., by stimulating or modulating immune cells. Further, the adjuvant compound enhances macrophage phagocytosis after binding the vaccine as a particulate (a carrier/vehicle function).

Adjuvant compounds useful in the present invention include Complete Freund's Adjuvant (CFA); Incomplete Freund's Adjuvant (IFA); Montanide ISA (incomplete seppic adjuvant); Ribi Adjuvant System (RAS); TiterMax; Syntex Adjuvant Formulation (SAF); Aluminum Salt Adjuvants; Nitrocellulose-adsorbed antigen; Encapsulated or entrapped antigens; Immunestimulating complexes (ISCOMs); and GerbuR adjuvant.

Methods of Immunization

The vaccines of the present invention have superior immunoprotective and immunotherapeutic properties over other vaccine lacking adjuvant polypeptides. Mucin-Ig fusion protein-containing vaccines have enhanced immunogenicity, safety, tolerability and efficacy. For example, the enhanced immunogenicity of the vaccine of the present invention may be greater than comparative non-adjuvant polypeptide-containing vaccines by 1.5-fold, 2-fold, 3-fold, 5-fold, 10-fold, 20-fold, 50-fold, 100-fold or more, as measured by stimulation of an immune response such as antibody production and/or secretion, activation and expansion of T cells, and cytokine expression (e.g., production of interleukins).

The cell surface of cancer cells often contains specific carbohydrates, polypeptides and other potential antibody epitopes that are not presence on the surface of non-cancerous cells. This antigen disparity allows the body's immune system to detect and respond to cancer cells. Mucin polypeptides have been associated with numerous cancers. For example, PSGL-1 has been associated with cancers, including lung cancer and acute myeloid leukemia (See Kappelmayer et al., Br J Haematol. 2001, 115(4):903-9). Also, MUC1-specific antibodies have been detected in sera from breast, pancreatic and colon cancer patients. It is clear that mucins can be recognized by the human immune system; therefore, immunity against tumor cells expressing specific antigens will be induced by vaccines containing mucin-Ig fusion proteins and a tumor cell-specific antigen. Immunity to tumor cells is measured by the extent of decrease of tumor size, decreased tumor vascularization, increased subject survival, or increased tumor cell apoptosis.

The invention provides a method of immunization of a subject. A subject is immunized by administration to the subject the vaccine including an adjuvant polypeptide and an antigen. The subject is at risk of developing or suffering from an infection, e.g., bacterial, viral or fungal. Infections include, Hepatitis C, HIV, Hepatitis B, Papilloma virus, Malaria, Tuberculosis, Herpes Simplex Virus, Chlamydia, or Influenza. Alternatively, is at risk of developing or suffering from cancer. The cancer is for example breast, lung, colon, prostate, pancreatic, cervical cancer or melanoma.

The methods described herein lead to a reduction in the severity or the alleviation of one or more symptoms of a infection or cancer. Infection and cancers diagnosed and or monitored, typically by a physician using standard methodologies A subject requiring immunization is identified by methods know in the art. For example subjects are immunized as outlined in the CDC's General Recommendation on Immunization (51(RR02) pp 1-36) Cancer is diagnosed for example by physical exam, biopsy, blood test, or x-ray.

The subject is e.g., any mammal, e.g., a human, a primate, mouse, rat, dog, cat, cow, horse, pig. The treatment is administered prior to diagnosis of the disorder. Alternatively, treatment is administered after diagnosis.

Efficaciousness of treatment is determined in association with any known method for diagnosing or treating the particular disorder Alleviation of one or more symptoms of the disorder indicates that the compound confers a clinical benefit. By "efficacious" is meant that the treatment leads to decrease in size, prevalence, or metastatic potential of the cancer in a subject. When treatment is applied prophylactically, "efficacious" means that the treatment retards or prevents a tumor from forming or retards, prevents, or alleviates a symptom the cancer. Assessment of cancer is made using standard clinical protocols. Similarly, increased immunization clinical benefit is determined for example by decreased physician visits, and decreased disease burden in the community.

Methods of Increasing Antibody Secretion

The invention provides a method of increasing or stimulating production and/or secretion of antibodies in a cell. The cell an antibody forming cell such as a B-cell. Alternatively, the cell is a cell that augmenst antibody production by a B cell such as a T-cell (Th and Tc), macrophage, dendritic cell Antibody secretion by a cell is increased by contacting the cell with the vaccine including an adjuvant polypeptide and an antigen. Antibody secretion by a cell can be increased directly, such as by stimulating B cells, or indirectly, such as by stimulating T cells (e.g., helper T cells), which activated T cells then stimulate B cells. Increased antibody production and/or secretion is measured by methods known to those of ordinary skill in the art, including ELISA, the precipitin reaction, and agglutination reactions.

Methods of Increasing Immune Cell Activation

The invention provides a method of activating or stimulating an immune cell (e.g., a B cell or a T cell). T cell activation is defined by an increase in calcium mediated intracellular cGMP, or an increase in cell surface receptors for IL-2. For example, an increase in T cell activation is characterized by an increase of calcium mediated intracellular cGMP and or IL-2 receptors following contacting the T cell with the vaccine, compared to in the absence of the vaccine. Intracellular cGMP is measured, for example, by a competitive immunoassay or scintillation proximity assay using commercially available test kits. Cell surface IL-2 receptors are measured, for example, by determining binding to an IL-2 receptor antibody such as the PC61 antibody. Immune cell activation can also be determined by measuring B cell proliferative activity, polyclonal immunoglobulin (Ig) production, and antigen-specific antibody formation by methods known in the art.

The invention will be further illustrated in the following non-limiting examples.

EXAMPLE 1

Production of Adjuvant Polypeptides

Construction of Expression Vectors.

The porcine $\alpha 1,3$ GT was PCR amplified from a pig spleen cDNA using a forward primer having six codons of complementary to the 5' end of the coding sequence, a Kozak translational initiation concensus sequence and a Hind3 restriction site, and a reverse primer with six codons of complementarity to the 3' end of the coding sequence, a translational stop and a Not I restriction site. The amplified $\alpha 1,3$GT cDNA was cloned into the polylinker of CDM8 using Hind3 and Not I. The P-selectin glycoprotein ligand-1 coding sequence was obtained by PCR from an HL-60 cDNA library, cloned into CDM8 with Hind3 and Not I, and confirmed by DNA sequencing. The mucin/immunoglobulin expression plasmid was constructed by ligating the PCR-amplified cDNA of the extracellular part of PSGL-1 in frame via a BamH I site, to the Fc part (hinge, CH2 and CH3) of mouse IgG2b carried as an expression casette in CDM7.

Transfections and Production of Secreted PSGL-1/mIgG$_{2b}$ Chimeras

The transfection cocktail was prepared by mixing 39 µl of 20% glucose, 39 µg of plasmid DNA, 127 µl dH$_2$O, and 15.2 µl 0.1 M polyethylenimine (25 kDa; Aldrich, Milwaukee, Wis.) in 5-ml polystyrene tubes. In all transfection mixtures, 13 µg of the PSGL-1/mIgG$_2$b plasmid was used. Thirteen micrograms of the plasmid for the different glycosyltransferases were added, and, when necessary, the CDM8 plasmid was added to reach a total of 39 µg of plasmid DNA. The mixtures were left in room temperature for 10 min before being added in 10 ml of culture medium to the cells, at approximately 70% confluency. After 7 days, cell supernatants were collected, debris spun down (1400×g, 15 mm) and NaN$_3$ was added to a final concentration of 0.02% (w/v).

Purification of Secreted PSGL-1/mIgG$_{2b}$, for SDS-PAGE and Western Blot Analysis PSGL-1/mIgG$_2$b fusion proteins were purified from collected supernatants on 50 µl goat anti-mIgG agarose beads (100:1 slurry; Sigma) by rolling head over tail overnight at 4° C. The beads with fusion proteins were washed three times in PBS and used for subsequent analysis. Typically, the sample was dissolved in 50 µl of 2× reducing sample buffer and 10:1 of sample was loaded in each well.

PNGaseF Treatment of Affinity-Purified PSGL-1/mIgG$_{2b}$

A PNGaseF kit (Roche Diagnostics, Indianapolis, Ind.) was used for N-glycan deglycosylation, A slight modification of the protocol provided by the manufacturer was used. In 1.5-ml Eppendorf tubes, 20 µl of reaction buffer was mixed with purified PSGL-1/mIgG$_2$b on agarose beads and boiled for 3 min. The mixture was spun down, and 10 µl of the supernatant was transferred to a new Eppendorf tube. Ten microliters of PNGaseF or, as a negative control, 10 µl of reaction buffer were added. The tubes were incubated for 1.5 h at 37° C. After incubation, 20 µl of 2× reducing sample buffer and 10 µl of H$_2$O was added, and the samples were boiled for 3 min.

ELISA for Determination of PSGL-1/mJgG$_2$b Concentration in Supernatants

Ninety-six-well ELISA plates (Costar 3590, Corning, N.Y.) were coated with 0.5 µg/well of affinity-purified goat anti-mIgG specific antibodies (Sigma) in 50 µl of 50 mM carbonate buffer, pH 9.6, for two h in room temperature. After blocking o/n at 4° C. with 300 µl 3% bovine serum albumin (BSA) in PBS with 0.05% Tween (PBS-T) and subsequent washing, 50 µl sample supernatant was added, serially diluted in culture medium. Following washing, the plates were incubated for 2 h with 50 µl of goat anti-mIgM-HRP (Sigma), diluted 1:10,000 in blocking buffer. For the development solution, one tablet of 3,3',5,5'-tetramethylbenzidine (Sigma) was dissolved in 11 ml of 0.05 M citrate/phosphate buffer with 3 µl 30% (w/v) H$_2$O$_2$. One hundred microliters of development solution was added. The reaction was stopped with 25 µl 2 M H$_2$SO$_4$. The plates were read at 450 and 540 nm in an automated microplate reader (Bio-Tek Instruments, Winooski, Vt.). As a standard, a dilution series of purified mIgG Fe fragments (Sigma) in culture medium was used in triplicate.

SDS-PAGE and Western Blotting

SDS-PAGE was run by the method of Laemmli (1970) with a 5% stacking gel and an 8% resolving gel, and separated proteins were electrophoretically blotted onto Hybond™-C extra membranes as described before (Liu et al., 1997). Following blocking overnight in Tris-buffered saline with 0.05% Tween-20 (TBS-T) with 3% BSA, the membranes were washed three times with TBS-T. They were then incubated for 1 h in room temperature with mouse anti-human blood group A all types (mIgM, Dako, Carpinteria, Calif.) or anti-human H type 1 (mIgG$_3$, Signet; Dedham, Mass.), H type 2 (mIgM, Dako) or H type 3 (mIgM, hybridoma HH14, ATCC HB9299). All antibodies were diluted 1:200 in 3% BSA in TBS-T, except for the H type 3 antibody, which was diluted to a concentration of 1 µg/ml in 3% BSA in TBS-T. The membranes were washed three times with TBS-T before incubation for 1 h at room temperature with secondary horseradish peroxidase (HRP)-conjugated antibodies, goat anti-mIgM (Cappel, Durham, N.C.) or goat anti-mIgG$_3$ (Serotec, Oxford, England) diluted 1:2000 in 3% BSA in TBS-T. Bound secondary antibodies were visualized by chemiluminescence using the ECL kit (Amersham Pharmacia Biotech, Uppsala, Sweden) according to the instructions of the manufacturer. For detection of the PSGL-1/mIgG$_2$b itself, HRP-labeled goat anti-mIgG (Sigma) was used at a dilution of 1:10,000 in 3% BSA in TBS-T as described, but without incubation with a secondary antibody.

Purification of Human IgG, IgM and IgA.

Human IgG, IgM and IgA were purified from human AB serum pooled from more than 20 healthy blood donors using goat anti-human IgG (Fc specific; A-3316, Sigma), IgM (µ-chain specific; A-9935, Sigma), and IgA (α-chain specific; A-2691, Sigma) agarose beads. Briefly, 5 ml of slurry (2.5 ml packed beads) were poured into a column (10 mm diameter) and washed with PBS. Ten milliters of human pooled AB serum was applied at 1 ml/minute using a peristaltic pump, washed with several column volumes of PBS, and eluted with 0.1 M glycine, 0.15 M NaCl, pH 2.4 using a flow rate of 1 ml/minute. One milliliter fractions were collected in tubes containing 0.7 ml of neutralizing buffer (0.2 M Tris/HCl, pH 9). The absorption at 280 nin was read spectrophotometrically and tubes containing protein were pooled, dialyzed against 1% PBS, and lyophilized. Lyophilized immunoglobulins were resuspended in distilled water and the concentrations adjusted to 16 mg/ml for IgG, 4 mg/ml for IgA and 2 mg/ml for IgM.

Expression and characterization of the PSGL1/m1gG2b fusion protein. Supernatants from COS-7 m6 cells transfected with the vector plasmid CDM8, the PSGL-1/mIgG2b plasmid, or the PSGL-1/mIgG2b together with the porcine α1,3GT plasmid, were collected approximately seven days after transfection. Secreted mucin/Ig fusion proteins were purified by absorption on anti-mouse IgG agarose beads and subjected to SDS-PAGE and Western blotting using the *Bandereia simplicifolia* isolectin B4 (BSA 1134) for detection. As seen in FIG. 1, the fusion protein migrated under reducing conditions as a broad band with an apparent molecular weight of 145 kDa that stained relatively poorly with silver. The heterogeneity in size, approximately 125 to 165 kDa, and poor stainability is in concordance with previous observations with respect to the behavior of highly glycosylated, mucin-type proteins. The fusion protein is most likely produced as a homodimer because SDS-PAGE under non-reducing conditions revealed a double-band of an apparent molecular weight of more than 250 kDa. The amounts of fusion protein affinity-purified from the two supernatants derived from the same number of COS cells transfected with the PSGL-1/mIgG2b plasmid alone or together with the α1,3 GT plasmid, respectively, were similar. Probing the electroblotted membranes with BSA 1134 revealed strong staining of the fusion protein obtained following cotransfection with the porcine α1,3GT (FIG. 1). The PSGL-1/mIgG2b fusion protein produced in COS-7 m6 cells without cotransfection of the α1,3 GT cDNA also exhibited weak staining with the BSA IB4 lectin, in spite of the fact that COS cells are derived from the Simian monkey, an old world monkey lacking α1,3 GT activity. This indicates that the BSA 1134 lectin has a slightly broader specificity than just Gal α1,3Gal epitopes. Nevertheless, cotransfection of the porcine α1,3GT cDNA supported the expression of a highly Gal α1,3Gal-substituted PSGL-1/mIgG2b fusion protein.

Figure 2A:
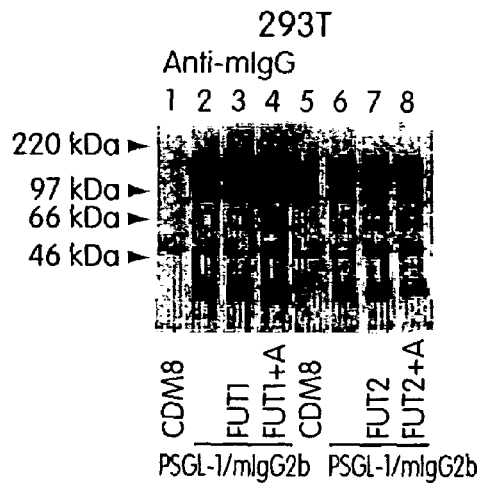
FIGS. 2A-E is a graph demonstrating the quantification by anti-mouse IgG Fc ELISA of the PSGL1/mIgG2b fusion protein concentration in increasing volumes of transfected COS cell supernatants before and after absorption on 50 pl of anti-mouse IgG agarose beads. Triplicate samples were analyzed.
Figure 2B:
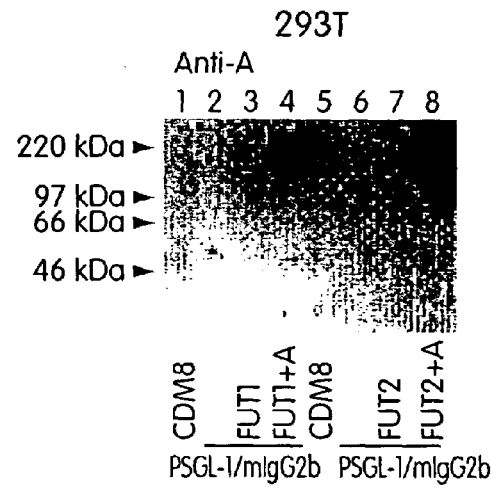
Figure 2C:
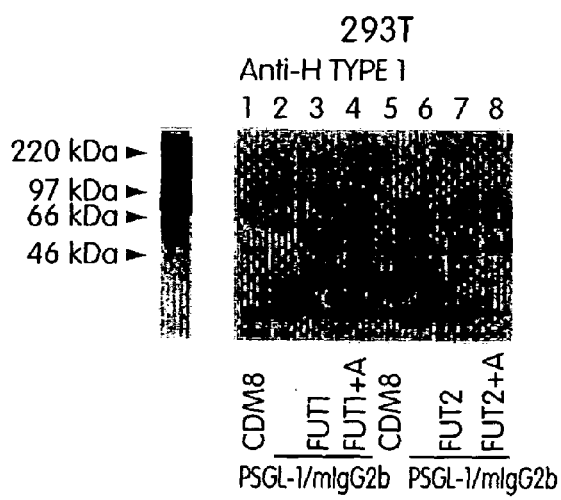
Figure 2D:
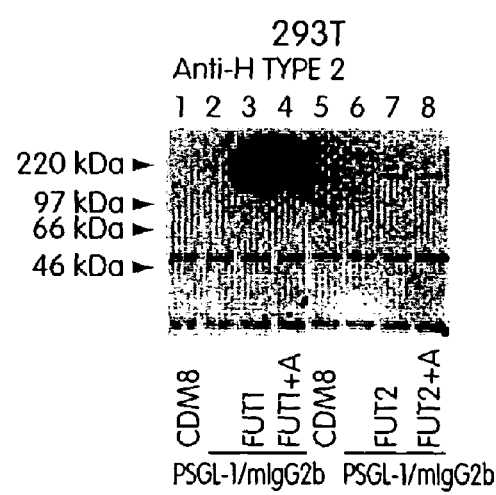
Figure 2E:
Figure 3A:
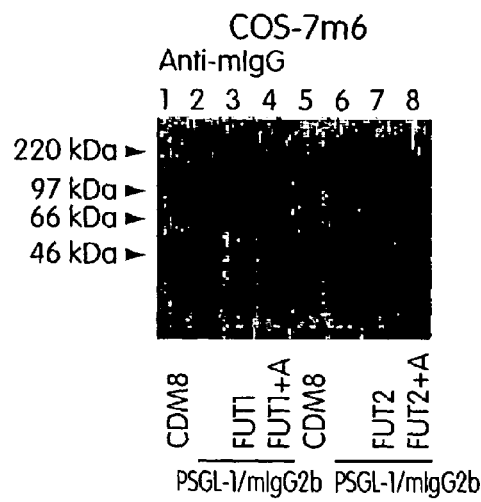
FIGS. 3A-E is a graph demonstrating antibody-dependent, complement-mediated PEC-A cell cytotoxicity by different volumes of human AB serum following absorption on 50 μl of anti-mouse IgG agarose beads carrying approximately 300 ng of Gal α1,3Gal- or non-substituted PSGL-1/mIgG2b as estimated in a $^{51}$Cr-release assay.
Figure 3B:
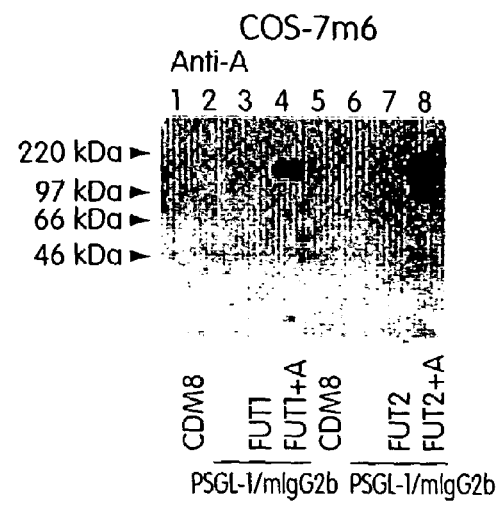
Figure 3C:
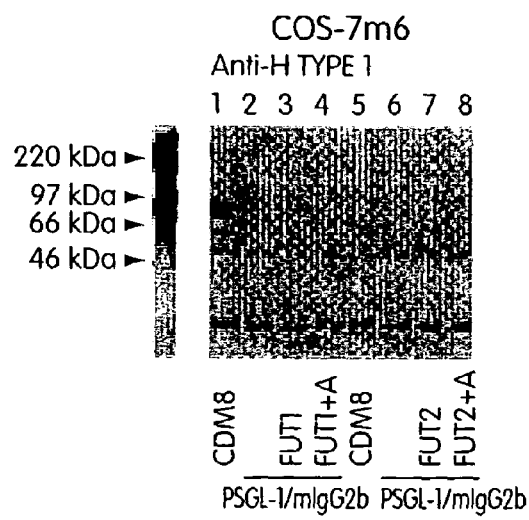
Figure 3D:
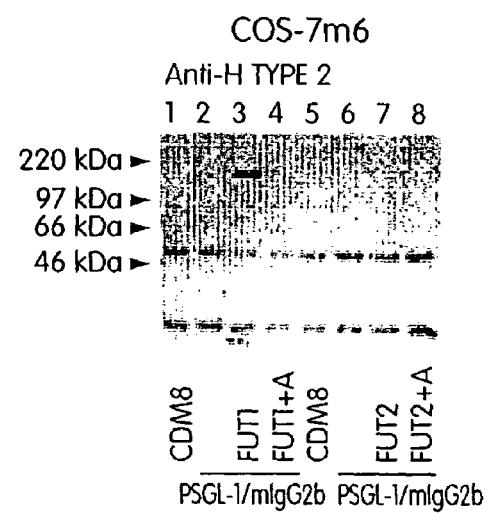
Figure 3E:
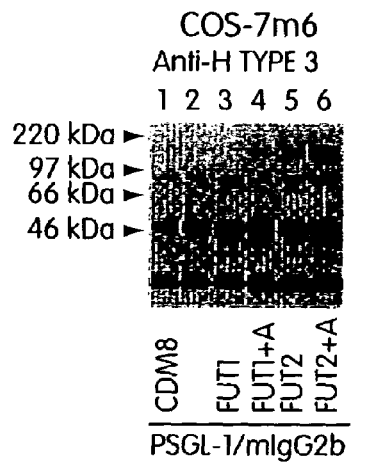
Figure 4A:
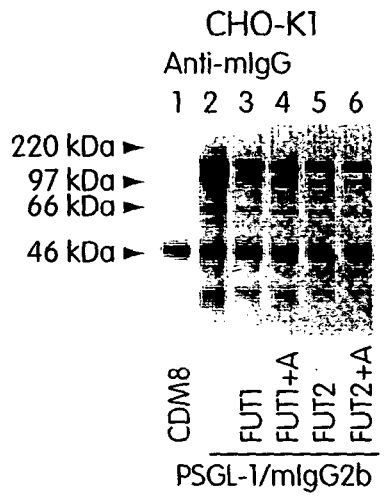
FIGS. 4A-E is a photograph of a ten percent SDS-PAGE of immunoaffinity purified human IgG, IgM, and IgA. Four micrograms of each sample were run under reducing and non-reducing conditions, and proteins were visualized by silver staining. The gel migration length of molecular weight proteins of 220, 97, 66, 46 and 30 kDa is indicated on the left hand side.
Figure 4B:
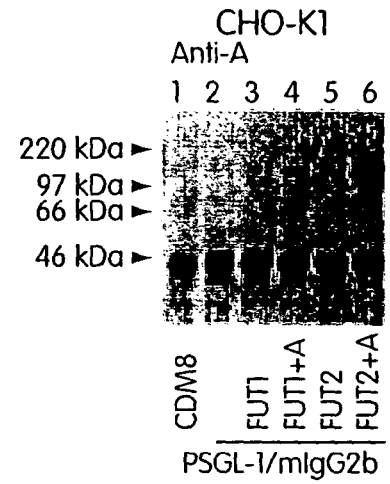
Figure 4C:
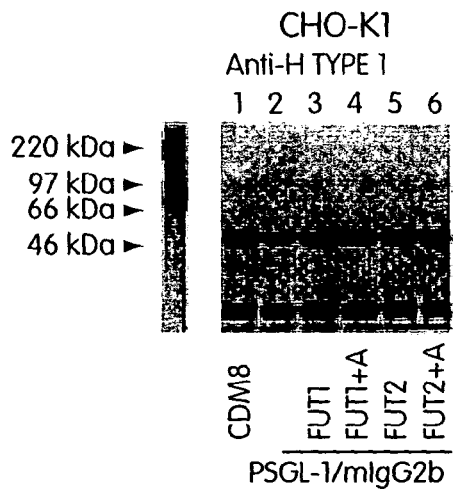
Figure 4D:
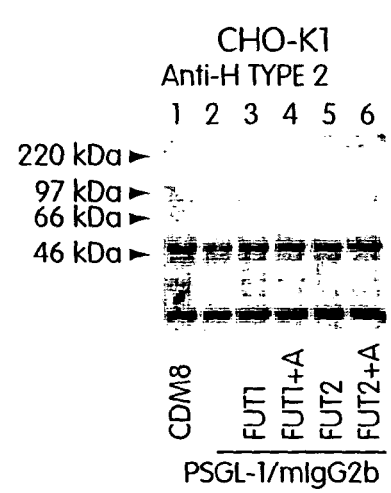
Figure 4E:
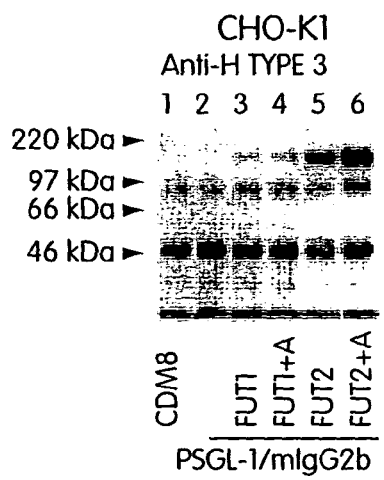
Figure 5:
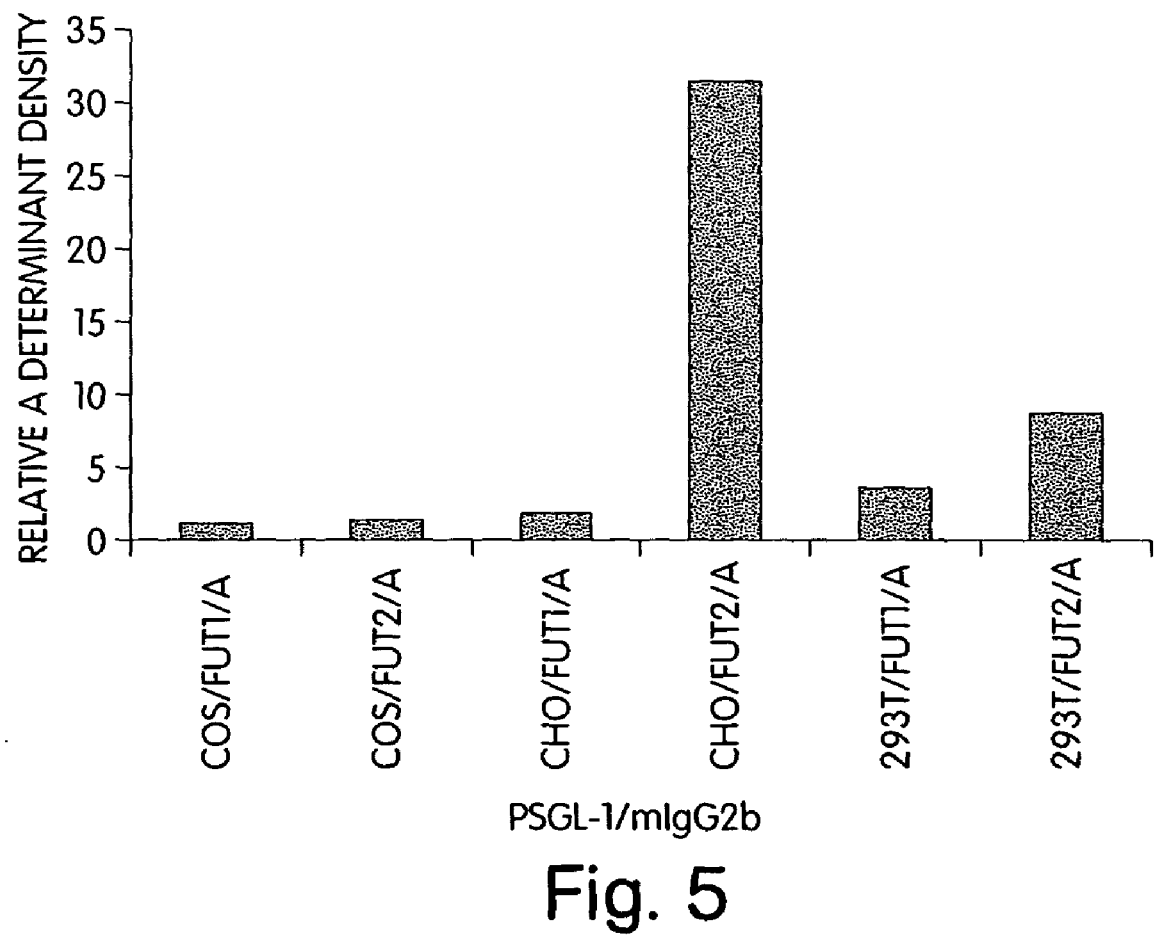
FIG. 5 is a graph demonstrating the antibody-dependent, complement-mediated PEC-A cell cytotoxicity of immunoaffinity purified human IgG, IgM and IgA before and after absorption on Galα1,3 Gal-substituted PSGLI/mIgG2b was investigated by $^{51}$Cr-release assays (right hand side Y-axis; % killing). The PEC-A cell binding of immunoaffinity purified IgG, IgM and IgA before and after absorption on Galα1, 3Gal-substituted PSGL-1/mIgG2b was estimated in a cell ELISA (left hand side Y-axis; O.D. at 405 nm). The two assays were run in parallel on absorbed and non-absorbed Ig fractions.

For quantification of PSGL-1/mIgG2b chimeras in supernatants of transfected COS cells, and on goat anti-mouse IgG agarose beads following absorption a sandwich ELISA was employed to quantify the amount of PSGL-1/mIgG2b in the supernatants of transfected COS cells. Typically, 5 culture flasks (260 ml flasks, Nunclon™) with COS cells at 70% confluence were transfected and incubated as described in materials and methods. Following an incubation period of seven days in 10 ml of AIM V medium per flask, the medium was collected. The concentration of fusion protein in the supernatant from such a transfection, as well as in different volumes of supernatant following absorption on 100 µl gel slurry of anti-mouse IgG agarose beads (corresponding to 50 µl packed beads) was determined by an ELISA calibrated with purified mouse IgG Fc fragments (FIG. 2). The concentration of PSGL-1/mIgG2b in the supernatants ranged from 150 to 200 ng/µl, and in this particular experiment it was approximately 160 ng/µl (FIG. 2A, the non-absorbed column). The concentration of PSGL-1/mIgG2b remaining in 2, 4 and 8 ml of supernatant following absorption on 50 µl packed anti-mouse IgG agarose beads was 32, 89 and 117 ng/µl, respectively. This corresponds to 260, 290 and 360 ng of PSGL-1/mIgG2b being absorbed onto 50 µl packed anti-mouse IgG agarose beads from 2, 4 and 8 ml of supernatant, respectively. Western blot analysis with the *B. simplicifolia* 1134 lectin revealed that 50 µl of packed beads could absorb out the PSGL1/mIgG2b fusion protein from 1 ml supernatant to below detectability and from 2 ml to barely detectable levels.

Abbreviations: BSA, bovine serum albumin; DXR, delayed xenorejection; ELISA, enzyme-linked immunosorbent assay; FT, fucosyltransferase; Gal, D-galactose; GT, galactosyltransferase; Glc, D-glucose; GlcNAc, D-N-acetylglucosamine; GlyCAM-1, glycosylation-dependent cell adhesion molecule-1; HAR, hyperacute rejection; Ig, immunoglobulin; MAdCAM, mucosal addressin cell adhesion molecule; PAEC, porcine aortic endothelial cells; P13MC, peripheral blood mononuclear cells; RBC, red blood cell; SDS-PAGE, sodium dodecyl sulphate polyacrylamide gel electrophoresis.

EXAMPLE 2

Production of PSGL-1/mIg-Ovalbumin Vaccines

The data described herein was generated using the following reagents and methods.

Cell culture: COS-7 m6 cells (Seed, 1987), CHO-K1 (ATCC CCL-61), and the SV40 Large T antigen expressing 293 human embryonic kidney cell line (293T; kindly provided by B. Seed), were cultured in Dulbecco's modified Eagle's medium (GibcoBrI, Life Technologies, Paisley, Scotland), supplemented with 10% fetal bovine serum (GibcoBrI, Life Technologies), 25 µg/ml gentamycin sulfate (Sigma, St. Louis, Mo.) and 2 mM glutamine (GibcoBrI, Life Technologies). The cells were passaged every 2-4 days. The HH14 hybndoma (ATCC HB-9299; U.S. Pat. No. 4,857,639) were cultured in RPMI 1640 (GibcoBrI, Life Technologies), supplemented with 10% fetal bovine serum, 100 U/ml of penicillin, 100 µg/µl of streptomycin, and 2 mM glutamine.

Materials. Crosslinker N-[γ-maleimidobutyryloxy] sulfosuccinnimide ester (Sulfo-GMBS) (22324, PIERCE, Rockford. Ill. 61105). Ovalbumin (A-7641, Sigma, St. Louis, Mo. 63178). Galα1,3Gal substituted PSGL1/mIgG2b. Coupling buffer: 20 mM sodium phosphate, 0.15 M NaCl, 0.1 M EDTA, pH 7.2 Hi Trap™ Desalting column (17-1408-01, Amersham Biosciences, SE-75184 Uppsala, Sweden). HiPrep™ 16/60 Sephacryl™ S-200 column (17-1166-01, Amersham Biosciences, SE-75184 Uppsala, Sweden).

Figure 6:
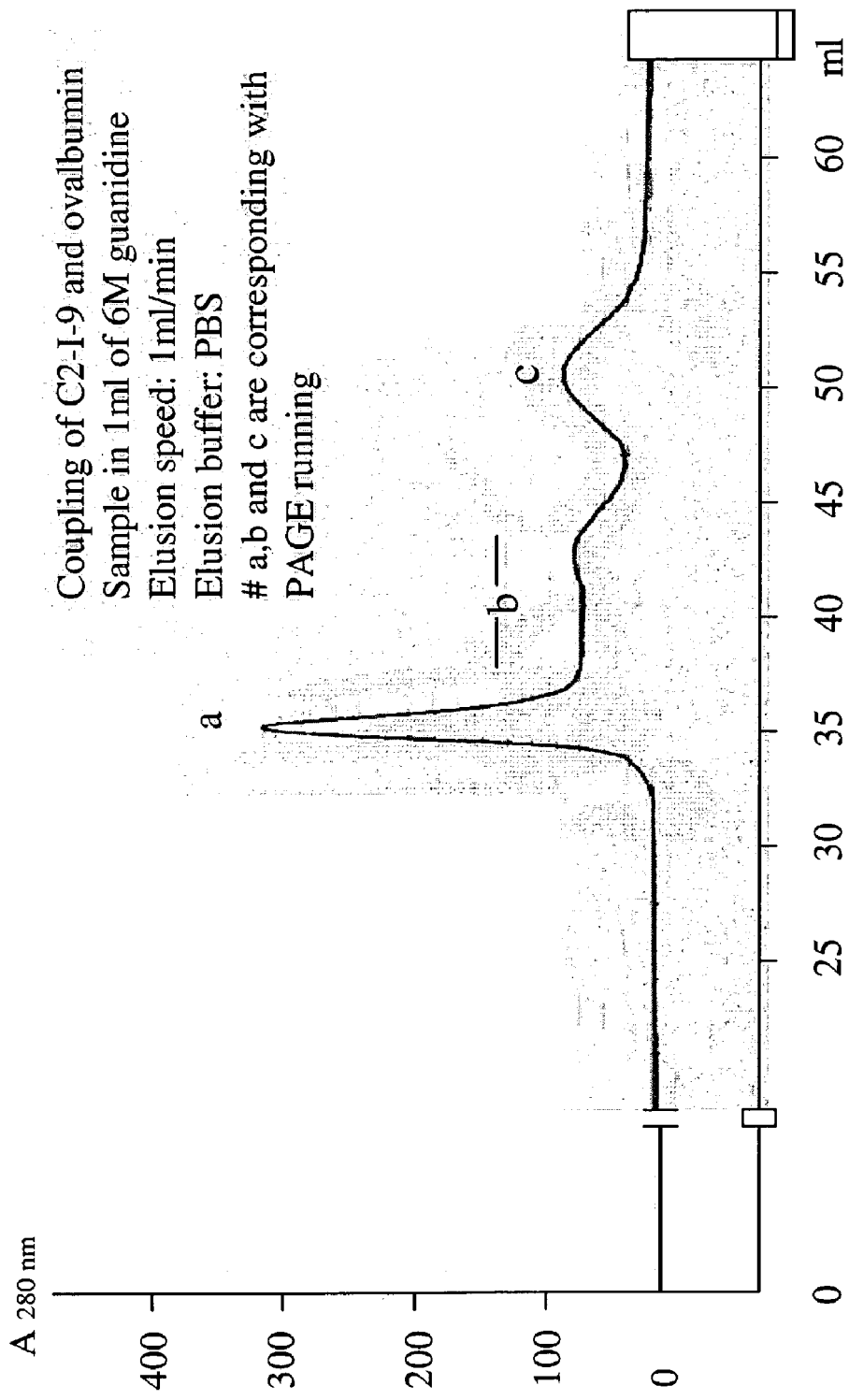
FIG. 6 is a chart showing the elution peak profile of ovalbumin to the adjuvant polypeptide of the invention.
Figure 7:
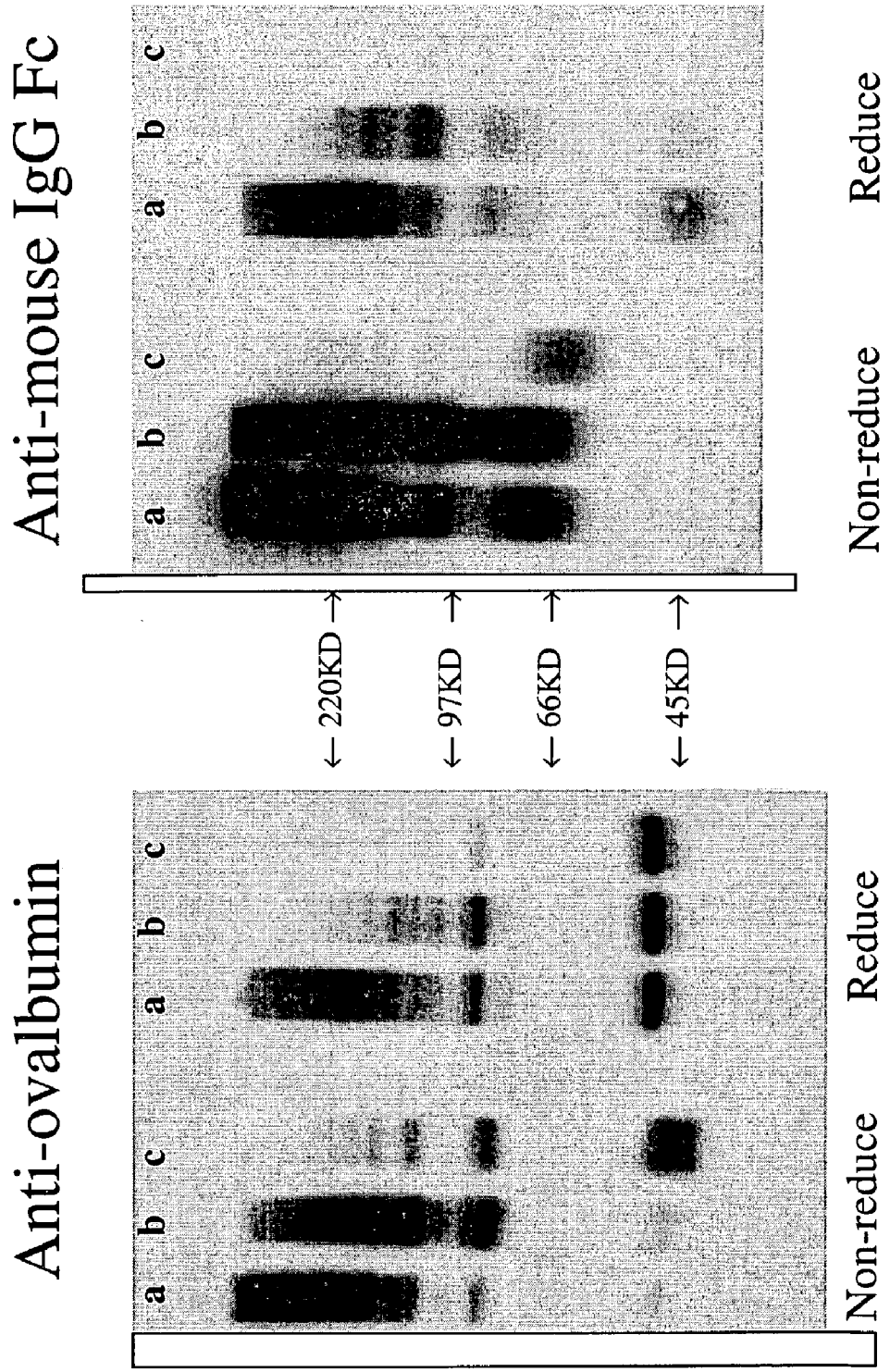
FIG. 7 is a photograph of a Western blot demonstrating the coupling of the antigen ovalbumin to the adjuvant polypeptide of the invention.

Vaccine production methods. The Galα1,3Gal substituted PSGLI/mIgG$_2$b described in Example 1 was resuspended in coupling buffer to a concentration of 2 mg/ml. 200 µl of resuspended Galα1,3Gal substituted PSGL1/mIgG$_2$b was transferred to a 10 ml tube. 2 mg of Sulfo-GMBS was dissolved in 1 ml of conjugation buffer, and 100 µl of the Sulfo-GMBS solution was immediately transferred into the test tube containing the Galα1,3Gal substituted PSGL1/mIgG$_{2b}$. Incubate for 2 hours in room temperature. Equilibrate the desalting column with 15 ml of coupling buffer. Apply the 300 µl of reaction solution onto the Hi Trap™ desalting column using an FPLC system. Elute with 0.5 ml aliquots of coupling buffer. Monitor the eluted protein by absorbance at 280 nm. The maleimide-activated Galα1,3Gal substituted PSGL1/mIgG$_2$b should elute in fraction 5-6. Dissolve 2 mg of ovalbumin in 500 µl of coupling buffer overnight at room temperature. Add ovalbumin solution to pooled fractions containing maleimide-activated Galα1,3Gal substituted PSGL1/mIgG2b. Incubate for 3 hours at room temperature. Add 8 M guanidine solution to the test tube containing the conjugated ovalbumin-PSGL-1/mIgG$_{2b}$ protein, until the concentration of guanidine reach 6 M. Equilibrate the HiPrep™ 16/60 Sephacryl™ S-200 column with 100 ml of PBS. Apply the 4.5 ml of reaction volume onto the column run in the FPLC system. Elute with 1.0 ml aliquots of PBS. Monitor the protein elution by absorbance at 280 nm. The coupling protein should elute in fraction 35-38 (see FIGS. 6 and 7). Dialyze against water to remove PBS. Freeze and lyophilize the coupling protein. Characterize the coupling protein by ELISA and Western blot analysis.

OTHER EMBODIMENTS

While the invention has been described in conjunction with the detailed description thereof, the foregoing description is intended to illustrate and not limit the scope of the invention, which is defined by the scope of the appended claims. Other aspects, advantages, and modifications are within the scope of the following claims.

What is claimed is:

1. A purified composition comprising:
   a dimerized fusion polypeptide comprising a first polypeptide linked to a second polypeptide, wherein the first polypeptide is a mucin polypeptide and is glycosylated by a α1,3 galactosyltransferase and the second polypeptide comprises at least a region of an immunoglobulin polypeptide covalently linked to a third polypeptide, wherein the third polypeptide is a viral polypeptide, a bacterial polypeptide or a parasitic polypeptide.

2. The composition of claim 1, wherein the first polypeptide comprises at least a region of a P-selectin glycoprotein ligand-1.

3. The composition of claim 1, wherein the first polypeptide comprises amino acids 19-319 of human P-selectin glycoprotein ligand-1 when numbered in accordance with wild type human P-selectin glycoprotein ligand-1.

4. The composition of claim 1, wherein the second polypeptide comprises a region of a heavy chain immunoglobulin polypeptide.

5. The composition of claim 1, wherein said second polypeptide comprises an Fc region of an immunoglobulin heavy chain.

6. The composition of claim 1, further comprising an adjuvant compound.

7. The composition of claim 1, wherein the viral polypeptide is selected from the group consisting of Hepatitis C, HIV, Hepatitis B, Papilloma virus, Herpes Simplex Virus, and influenza.

* * * * *